United States Patent
Bosley et al.

[11] Patent Number: 5,773,266
[45] Date of Patent: Jun. 30, 1998

[54] IMMOBILIZED LIPASES ON A DRY, POROUS PARTICULATE HYDROPHOBIC SUPPORT AND CONTAINING A NON-IONIC SURFACTANT

[75] Inventors: John Anthony Bosley, Islip; Stephen Raymond Moore, Thrapston, both of United Kingdom

[73] Assignee: Loders-Croklaan B.V., Wormerveer, Netherlands

[21] Appl. No.: 545,818

[22] PCT Filed: Apr. 22, 1994

[86] PCT No.: PCT/EP94/01308

§ 371 Date: Nov. 9, 1995

§ 102(e) Date: Nov. 9, 1995

[87] PCT Pub. No.: WO94/28118

PCT Pub. Date: Dec. 8, 1994

[30] Foreign Application Priority Data

May 20, 1993 [EP] European Pat. Off. ............... 93303917

[51] Int. Cl.$^6$ .............................. C12P 7/64; C12N 11/14; C12N 11/08; C12N 9/20
[52] U.S. Cl. .......................... 435/134; 435/176; 435/177; 435/180; 435/198
[58] Field of Search .................................... 435/134, 176, 435/177, 180, 198

[56] References Cited

U.S. PATENT DOCUMENTS

| | | | |
|---|---|---|---|
| 4,539,294 | 9/1985 | Metcalfe et al. | 435/180 |
| 4,629,742 | 12/1986 | Brady et al. | 521/55 |
| 5,232,843 | 8/1993 | Bosley et al. | 435/135 |

FOREIGN PATENT DOCUMENTS

| | | |
|---|---|---|
| 0 322 213 | 6/1989 | European Pat. Off. . |
| 0 514 694 A1 | 11/1992 | European Pat. Off. . |
| 2 676 451 | 11/1992 | France . |

OTHER PUBLICATIONS

Mosbach et al, Methods in Enzymology, vol. 135, Part B, pp. 230–252 (1987).

Chemical Abstracts, vol. 118, No. 25, Abstract No. 250676n (Jun. 21, 1993).

Database WPI, Derwent Publications, Ltd., An 89–051780.

*Primary Examiner*—David M. Naff
*Attorney, Agent, or Firm*—Pillsbury Madison & Sutro LLP

[57] ABSTRACT

Immobilized lipases are prepared containing lipase bound to a dry, porous particulate hydrophobic support having an average pore size of 0.05–5 μm. Preparation is carried out by contacting the hydrophobic support with an aqueous solution of the lipase and with a non-ionic surfactant containing at least one fatty acid and having an HLB-value of at least 8 to provide a supported lipase, washing the supported lipase and drying the washed supported lipase to obtain the immobilized lipase. The lipase may be obtained from *Candida Antarctica* β, *Rhizomucor miehei*, Humicolo or *Candida Rosa*, and be a lipase specific for esterification of fatty acids with alcohol, 1,3-specific or randomizing transesterification lipase or lipase specific for the hydrolysis of partial glycerides, esters or triglycerides. The surfactant may be present in the aqueous solution of lipase in a concentration of 0.01–10 wt. %, and preferred surfactants are a polyoxyethylene sorbitan fatty acid ester and a polyglycerol fatty acid ester. The support may be a aliphatic olefinic polymer such as polyethylene or polypropylene, a homo- or copolymer of styrene or a blend thereof or a pre-treated inorganic support. The immobilized lipases are used for hydrolysis of triglycerides, diglycerides or esters or for the esterification or transesterification of fatty acids, diglycerides or triglycerides.

15 Claims, No Drawings

IMMOBILIZED LIPASES ON A DRY, POROUS PARTICULATE HYDROPHOBIC SUPPORT AND CONTAINING A NON-IONIC SURFACTANT

BACKGROUND OF THE INVENTION

This application is a 371 of international application PCT/EP94/01308, filed Apr. 22, 1994.

Enzymic conversions of triglycerides, diglycerides, monoglycerides, alkyl esters or free fatty acids, both for the production of triglycerides or other esters and for the hydrolysis of these compounds, in particular for the production of free fatty acids and of free alcohols or glycerol, have been known for many years.

GB 1,577,933, e.g., discloses a process for the preparation of triglycerides by interesterification of a mixture of triglycerides or by reaction of a triglyceride with a free fatty acid. Enzymes that can be used are randomizing enzymes; 1,3-specific enzymes; site-specific enzymes, such as $\Delta^9$-cis specific enzymes etc. The enzymes can be supported on support materials, which enable the application of continuous processes, while simultaneously increasing the activity of the enzymes.

According to U.S. Pat. No. 4,629,742 or EP 322,213, an improvement can be achieved, in particular with respect to enzyme activity, when the enzyme, preferably a lipase, is supported on a hydrophobic support material with a specific pore diameter (i.e. above 50 μm). However, the process for the immobilization of the enzyme requires pre-treatment of the hydrophobic support with a polar organic solvent, if the best results are to be achieved.

According to EP 424,130, a further improvement in enzyme stability can be obtained when the hydrophobic support is pre-treated with alcohol, followed by adsorption of a non-lipase protein, prior to the lipase adsorption.

EP 514,694 discloses an immobilization of lipase on a carrier whereby a surface active agent is added to the lipase-solution to make a micelle around the lipase. The surface active agent can be a non-ionic surface active agent. However no limitations are given for this agent.

We have performed a study in order to find out whether such a solvent pre-treatment could be avoided. Another aim of this study was to find out whether the lipase enzyme could be immobilized by a less complicated process, avoiding any pre-treatment, whereby an in situ immobilization could be achieved in the reaction column per se.

This study has resulted in our invention, which comprises a new process for the immobilization of lipases, resulting in new immobilized lipase enzyme compositions having an enzyme activity that is comparable with that of the prior art products.

SUMMARY OF THE INVENTION

Accordingly, our invention concerns in the first instance a process for the preparation of immobilized lipase enzymes on a dry, porous particulate hydrophobic support material having an average pore size of 0.05–5 μm, wherein the hydrophobic support is contacted with an aqueous solution of the lipase enzyme, either after the support is contacted with a non-ionic surfactant containing at least one fatty acid moiety and having an HLB (=hydrophilic lipophilic balance) value of at least 8, or simultaneously during the contact with the lipase or prior to the contact of the support with the surfactant, whereupon the supported lipase is washed and the washed material is dried.

It is emphasized here that the surfactant can either be completely dissolved in the waterphase (forming a clear solution) or can form a stable dispersion in the waterphase (forming a hazy or an opaque dispersion). This is disclosed in Porter's Handbook of Surfactants 1991, page 42 Ed: Blackie.

From U.S. Pat. No. 4,539,294 it is known that long chain cationic surfactants can be used in the immobilization of lipases. As supports hydrophobic supports, such as Accurel® are mentioned. However, according to this process a solution of the surfactant in a polar organic solvent must be applied.

According to the process of our invention, the support should be contacted with an aqueous solution of the lipase enzyme while the non-ionic surfactant is to be used at any stage of this contact in order to achieve the required loading and enzyme activity.

As the simplest process is one in which this contact is established simultaneously with the contact with the lipase enzyme, a preference is expressed for a process wherein the aqueous lipase solution also contains the surfactant. In this way, a separate pre-treatment step can be avoided because immobilization can now occur in a column loaded with the hydrophobic support material by passing this solution through the column in the absence of any other reactant (=triglyceride etc.).

Surprisingly it was found, that enzyme loading of the support leading to loaded, supported enzymes, which displayed esterification activity only occurred when our non-ionic surfactants, containing at least one fatty acid moiety and having an HLB-value of at least 8.0 were applied in the immobilization process. Application of surfactants, based on non-ionic ethers or of anionic or cationic surfactants either led to a loading of zero or to a loaded immobilized enzyme without significant esterification activity.

DETAILED DESCRIPTION OF THE INVENTION

The lipase that can be applied in the above-mentioned process is any of the known lipases, so lipases specific for the esterification of fatty acids with alcohols, such as *Candida Antarctica* β or 1,3-specific lipases or randomizing transesterification lipases, such as Humicola species, or lipases specific for the hydrolysis or synthesis of partial glycerides, such as Amano G lipase or lipases specific for the hydrolysis of esters or triglycerides, such as *Candida rugosa* but also $\Delta^9$-specific lipases can be applied. Examples of these lipases are mentioned in the references cited above.

The hydrophobic support material can be any of the hydrophobic supports mentioned in U.S. Pat. No. 4,629,742, EP 322,213 or EP 424,130. These supports can therefore be selected from aliphatic olefinic polymers, oxidation polymers, blends of these polymers or pre-treated inorganic supports in order to make these supports hydrophobic. This pre-treatment preferably comprises silanization with an organic silicon compound, the inorganic material being preferably silica, alumina, glass or ceramics.

The preferred supports, however, are made from polystyrene, copolymers of styrene, polyethylene, polypropylene or from co-polymers derived from (meth)acrylates.

The non-ionic surfactant has an HLB of more than 8, preferably 8–20. The surfactant can, be formed from sugars, (both mono-di-and polysaccharides), polyols (e.g. sorbitan and sorbitol) or polyethylene glycol as the hydrophylic part of the surfactant. The other part of the non-ionic surfactant must be a fatty acid moeity. Examples thereof being saturated straight chain fatty acids with 8–22 C-atoms. Very suitable non-ionic surfactants are polyoxyethylene sorbitan fatty acid esters, in particular those derived from lauric acid, such as Tween 20®.

Although the lipase concentration in the aqueous solution is not critical and can be any concentration up to the saturation concentration, a preference is expressed for the use of an enzyme concentration that results in an enzyme concentration of 1–20 wt. %, based on the support material, in the immobilized lipase. Such lipase concentrations can result in loadings (in KLU/g) of 1–1500 KLU/g, in particular 20–100 KLU/g.

The surfactant concentration in the aqueous solution should be sufficient to ensure effective loading of the support by the enzyme. Very good results were obtained by applying an aqueous solution with a surfactant concentration of at least 0.01 wt %, preferably 0.01–10, most preferably 0.1–5 wt. %. Although more than 10 wt % surfactant could be used, no advantages are obtained. As stated before, this surfactant solution can also contain the dissolved lipase enzyme, which can be present up to its saturation concentration.

The contact times applied can vary between wide ranges. Suitably, however, contact times between 1 and 72 hours are applied.

Immobilization of the lipase can be performed in many different ways. Suitably, the contact between support, lipase enzyme and/or surfactant is performed as a batch process, as a continuous process in a fixed bed, as a continuous process in a fluidized bed or in a continuously stirred tank, while the contacting is performed with a continuous motion of the lipase solution.

Although the water content of the hydrophobic support used for the immobilization is not critical and will usually be very low, it was found that the best results are obtained when this water content is less than 1 wt. %.

Application of the above-mentioned process results in the production of new immobilized lipase enzymes. In these new supported enzymes, a small amount of our non-ionic surfactant is always present. These new immobilized lipase enzymes are also part of the invention.

Therefore, our invention also concerns an immobilized lipase enzyme on a hydrophobic, porous, dry particulate material having an average pore size of 0.05–5 $\mu$m, wherein the immobilized supported enzyme material also contains 0.0001–5 wt. % of a non-ionic surfactant containing at least one fatty acid moiety and having an HLB value of at least 8.0, most preferably of 8–20, and having a water content of preferably less than 10 wt. %.

The surfactant is a nonionic material; preferred surfactants are polyoxyethylene sorbitan fatty acid esters (Tweens ®), in particular Tween 20®, which is derived from lauric acid. However, also polyglycerol fatty acid esters are suitable.

The enzyme concentration in the immobilized lipase enzyme is preferably 1–20 wt. % (which can result in enzyme loadings of 1–1500 KLU/g).

Although the lipase enzyme can be any prior art lipase, a preference is expressed for immobilized lipase enzyme material, wherein the enzyme is selected from 1) enzymes specific for the esterification of fatty acids with alcohol, preferably *Candida Antarctica* β, 2) 1,3-specific or randomizing transesterification enzymes, preferably *Rhizomucor miehei* and *Humicola* species, 3) enzymes specific for the hydrolysis of partial glycerides, preferably Amano G, and 4) enzymes specific for the hydrolysis of esters or triglycerides, preferably *Candida rugosa*.

The support material can be selected from any of the prior art hydrophobic supports. However, a preference exists for supports selected from immobilized lipase enzyme material wherein the hydrophobic support is selected from aliphatic olefinic polymers;

homo- and copolymers of styrene;

oxidation polymers;

blends of these polymers;

pre-treated inorganic supports, preferably silanized inorganic support, such as silica, alumina, glass or ceramics.

The best immobilized lipase enzymes are obtained when the support material is a co-or homopolymer of styrene, a polyethylene or polypropylene polymer.

A definition for the hydrophobicity of a support can be found in U.S. Pat. No. 4,629,742 and should be regarded as being included here as well. In practice, this definition means that a hydrophobic support material hardly adsorbs any water when in contact therewith.

EXAMPLES

I. Immobilization of *Candida Antarctica* β using Tween 20

A) Immobilization in the Presence of Tween 20

Accurel® EP100 (0.5 g) was placed in a flask and phosphate buffer (100 ml, 0.01M, pH 7) containing Tween 20 (0.65 g) and *Candida Antarctica* β lipase (61 mg) was added. The immobilization process was monitored by measuring the activity of the solution. All of the lipase in the solution was adsorbed on to the Accurel®. After 16 hours, the biocatalyst was washed and dried.

B) Pre-wetting with Tween 20

Accurel® EP100 (0.5 g) was placed in a flask and phosphate buffer (30 ml, 0.01M, pH 7) containing Tween 20 (0.65 g) was added. After 20 minutes, phosphate buffer (100 ml) containing *Candida Antarctica* β lipase (61.5 mg) was added and the immobilization process carried out. All of the lipase added was adsorbed. The biocatalyst was washed and dried.

II. Activity Measurements

The esterification activity (standard octyl oleate synthesis) was determined and compared to a control catalyst prepared with ethanol wetting of the support according to U.S. Pat. No. 4,629,742.

| Example | Loading (KLU/g) | Activity (micromoles/min./mg |
|---------|-----------------|------------------------------|
| I A     | 21.0            | 4.9                          |
| I B     | 21.2            | 4.6                          |
| Control | 16.1            | 4.5                          |

The loading was assessed by loss of lipase activity from the enzyme solution, as set out in EP 322,213.

III. Comparing Different Non-ionic Surfactants

Accurel EP 100 (1.0 g) was placed in a flask and phosphate buffer (50 ml, 0.01M, pH7) containing surfactant (0.25 g) and Humicola lipase (0.4 ml, 40,000 LU Lipolase 100 T) was added. After 16 hours the amount of lipase adsorbed was determined by measuring the lipase activity in the supernatant solution. After washing repeatedly in distilled water (4×300 ml) the catalyst was dried under vacuum at room temperature and its esterification activity determined using the octyl oleate synthesis assay.

1. Esters

| Surfactant | HLB | Lipase loading KLU/g | Esterification acitivity μmoles/min/mg |
|---|---|---|---|
| TWEEN 20 | 16.7 | 32.8 | 0.14 |
| TWEEN 65 | 10.5 | 27.9 | 0.20 |
| TWEEN 80 | 15.0 | 31.8 | 0.27 |
| TWEEN 85 | 11.0 | 34.1 | 0.21 |
| PEG 400 Monostearate | 11.2 | 22.5 | 0.15 |

2. Comparative examples; using non-ionics based on ethers

| Surfactant | HLB | Lipase loading KLU/g | Esterification activity μmoles/min/mg |
|---|---|---|---|
| SYNPERONIC NP5 | 10.5 | 24.5 | 0 |
| SYNPERONIC NP10 | 13.3 | 35.1 | 0 |
| SYNPERONIC NP30 | 17.1 | 34.5 | 0 |
| BRIJ 30 | 9.7 | 0 | 0 |
| BRIJ 35 | 16.9 | 0 | 0 |
| BRIJ 56 | 12.9 | 0 | 0 |
| BRIJ 76 | 12.4 | 0 | 0 |
| Nonidet P40 | — | 27.8 | 0 |

Comparative Example IV

Accurel EP100 (1.0 g) was placed in a flask and phosphate buffer (50 ml, 0.01M, pH7) containing surfactant (0.25 g) and Humicola lipase (0.4 ml, 40,000 LU, Lipolase 100T) was added. After 16 hours the amount of lipase adsorbed was determined by measuring the lipase activity in the supernatant solution. After washing repeatedly in distilled water (4×300 ml) the catalyst was dried under vacuum at room temperature and its esterification activity determined using the octyl oleate synthesis assay.

1. Anionics

| Surfactant | Lipase Loading KLU/g | Esterification acitivity μmoles/min/mg. |
|---|---|---|
| AOT[1] | 7.4 | 0 |
| SDS[2] | 0 | 0 |
| Sodium laurate | 5.7 | 0 |

[1]AEROSOL OT
[2]Sodium dodecyl sulphate

2. Cationics

As above except that the buffer used was Tris/HCl, 0.01M, pH7.

| | | |
|---|---|---|
| CTAB[1] | 21.0 | 0 |
| Dodecylamine | 25.5 | 0 |

[1]Cetyl trimethylammonium bromide

Example V

Accurel EP100 (1.0 g) was placed in a flask and phosphate buffer (100 ml, 0.01M, pH 7) containing TWEEN 20 (0.5 g) and lipase (see table) was added. After 16 hours the amount of lipase adsorbed was determined by measuring the lipase activity in the supernatant solution. After washing repeatedly in distilled water (4×300 ml) the catalyst was dried under vacuum at room temperature and its esterification activity determined using the octyl oleate synthesis assay.

| Lipase | Lipase added KLU | Lipase loading KLU/g | Esterification activity μmoles/min/mg |
|---|---|---|---|
| Humicola[1] | 87.2 | 83.3 | 1.18 |
| Rhizomucor miehei[2] | 21.9 | 19.2 | 0.70 |
| Candida antarctica B[3] | 21.0 | 21.0 | 4.86 |

[1]Lipolase 100T, 1.0 ml, 85 KLU/ml
[2]Lipozyme 10,000L, 2.0 ml, 10.5 KLU/ml
[3]SP 434, 60 mg, 180 KLU/g
All lipases ex Novo-Nordisk

Example VI

Non-ionic surfactants, co-immobilisation

C. Surfactant concentration

Method

Accurel EP100 (1.0 g) was placed in a flask and phosphate buffer (50 ml, 0.01M, pH7) containing TWEEN 20 (see Table) and Humicola lipase (0.45 ml, 43,000 LU, Lipolase 100T) was added. After 16 hours the amount of lipase adsorbed was determined by measuring the lipase activity in the supernatant solution. After washing repeatedly in distilled water (4×300 ml) the catalyst was dried under vacuum at room temperature and its esterification activity determined using the octyl oleate synthesis assay.

| Surfactant concentration % w/v solution | Lipase loading KLU/g | Esterification activity μmoles/min/mg |
|---|---|---|
| 0 | 0 | 0 |
| 0.042 | 9.6 | 0.01 |
| 0.140 | 22.2 | 0.12 |
| 0.350 | 40.4 | 0.24 |
| 0.5 | 38.1 | 0.33 |
| 0.7 | 40.7 | 0.42 |
| 1.4 | 37.5 | 0.41 |

Example VII

Non-ionic surfactants, co-immobilisation

D. Support type

Method

Support (1.0 g) was placed in a flask and phosphate buffer (50 ml, 0.01M, pH 7) containing TWEEN 20 (0.25 g) and Humicola lipase (0.45 ml, 43,000 LU, Lipolase 100T) was added. After 16 hours the amount of lipase adsorbed was determined by measuring the lipase activity in the supernatant solution. After washing repeatedly in distilled water (4×300 ml) the catalyst was dried under vacuum at room temperature and its esterification activity determined using the octyl oleate synthesis assay.

| Support | wt. surfactant g. | lipase loading KLU/g | Esterification activity μmoles/min/mg |
|---|---|---|---|
| Polystyrene[1] | 0 | 18.0 | 0.13 |
| Polystyrene[1] | 0.25 | 39.6 | 0.66 |

| Support | wt. surfactant g. | lipase loading KLU/g | Esterification activity µmoles/min/mg |
|---|---|---|---|
| Hydrophobic silica[2] | 0 | 0 | 0 |
| Hydrophobic silica[2] | 0.25 | 39.7 | 0.22 |

[1]D2479, Macroporous polystyrene supplied by Purolite Ltd., UK
[2]XWP 1500, macroporous silica supplied by Grace, UK. Rendered hydrophobic by treatment with dichlorodimethylsilane.

Example VIII

Surfactant type, pre-wetting

Method

Accurel EP100 (2.0 g) was placed in a flask and phosphate buffer (100 ml, 0.01M, pH 7) containing surfactant (0.5 g) was added. After 16 hours of gentle stirring the support was separated by filtration and washed with distilled water (1000 ml). The wet support was placed in a flask and to this was added phosphate buffer (200 ml, 0.01M, pH 7) containing Humicola lipase (Lipolase 100 T, 180 KLU). The amount of lipase adsorbed was determined by measuring the lipase activity in the supernatant solution. After 16 hours the catalyst was washed in distilled water (4×300 ml) and dried under vacuum at room temperature.

The activity of the catalyst was determined using the octyl oleate assay.

1. Esters

| Surfactant | HLB | Lipase loading KLU/g | Esterification activity µmoles/min/mg |
|---|---|---|---|
| TWEEN 20 | 16.7 | 91.1 | 1.15 |
| TWEEN 65 | 10.5 | 76.9 | 1.01 |
| TWEEN 80 | 15.0 | 76.6 | 1.29 |

2. Ethers

| Surfactant | HLB | Lipase loading KLU/g | Esterification activity µmoles/min/mg |
|---|---|---|---|
| BRIJ 30 | 9.7 | 0 | 0 |
| BRIJ 35 | 16.9 | 69.3 | 0 |
| SYNPERONIC NP30 | 17.1 | 88.5 | 0 |

Surfactants - Chemical composition and manufacturers

| Surfactant | Chemical composition[1] | Manufacturer[2] |
|---|---|---|
| BRIJ 30 | Polyoxyethylene (4) lauryl ether | Atlas Powder |
| BRIJ 35 | Polyoxyethylene (23) lauryl ether | Atlas Powder |
| BRIJ 56 | Polyoxyethylene (10) cetyl ether | Atlas Powder |
| BRIJ 76 | Polyoxyethylene (10) stearyl ether | Atlas Powder |
| SYNPERONIC NP5 | Polyoxyethylene (10) nonylphenyl ether | I.C.I. |
| SYNPERONIC NP10 | Polyoxyethylene (10) nonylphenyl ether | I.C.I. |
| SYNPERONIC NP30 | Polyoxyethylene (30) nonylphenyl ether | I.C.I. |
| Nonidet P40 | Polyoxyethylene nonylphenyl ether | Shell Chemicals |
| TWEEN 20 | Polyoxyethylene (20) sorbitan monolaurate | Atlas Chemicals |
| TWEEN 65 | Polyoxyethylene (20) sorbitan tristearate | Atlas Chemicals |
| TWEEN 80 | Polyoxyethylene (20) sorbitan monooleate | Atlas Chemicals |
| TWEEN 85 | Polyoxyethylene (20) sorbitan trioleate | Atlas Chemicals |
| PEG 400 Monostearate | Polyethylene glycol 400 monostearate | Supplied by Unichema BV |
| Aerosol OT | Dioctyl ester of sodium sulphosuccinic acid | Supplied by BDH, Poole, UK |

[1]Figure in brackets is the number of repeat units in the polyoxyethylene chain
[2]Unless otherwise indicated all surfactants were supplied by Fluka Chemicals, UK.

We claim:

1. Immobilized lipase on a hydrophobic, porous, dry particulate material having an average pore size of 0.05–5 µm, wherein the immobilized lipase on the hydrophobic, porous, dry particulate material contains 0.0001–5 wt. % of a non-ionic surfactant, with an HLB-value of at least 8.0, and containing at least one fatty acid moiety and wherein the immobilized lipase has a water content of less than 10 wt. %.

2. Immobilized lipase according to claim 1, wherein the surfactant is a polyoxyethylene sorbitan fatty acid ester or a polyglycerol fatty acid ester.

3. Immobilized lipase according to claim 1, wherein the lipase concentration is 1–20 wt. %, based on the support material.

4. Immobilized lipase according to claim 1, wherein the lipase is selected from 1) lipase specific for the esterification of fatty acids with alcohol, 2) 1,3-specific or randomizing transesterification lipase, 3) lipase specific for the hydrolysis of partial glycerides, and 4) lipase specific for the hydrolysis of esters or triglycerides.

5. Immobilized lipase according to claim 1 wherein the hydrophobic support is selected from
    aliphatic olefinic polymers;
    homo- or copolymers of styrenes;
    blends of aliphatic olefinic polymers and homo- or copolymers of styrene; and
    pre-treated inorganic supports.

6. Immobilized lipase according to claim 5, wherein the aliphatic olefinic polymer is polyethylene or polypropylene.

7. Immobilized lipase according to claim 4 wherein the lipase is obtained from *Candida Antarctica* β, *Rhizomucor miehei*, Humicolo or *Candida Rosa*.

8. Immobilized lipase according to claim 5 wherein the pre-treated inorganic support is a silanized inorganic support.

9. Process for either the hydrolysis of triglycerides, diglycerides or esters, or for the esterification or transesterification of fatty acids or diglycerides or triglycerides, which comprises performing the hydrolysis, esterification or transesterification in the presence of an immobilized supported lipase according to claim 1.

10. Process for the preparation of immobilized lipase on a dry, porous particulate hydrophobic support material having an average pore size of 0.05–5 µm which comprises contacting the hydrophobic support with an aqueous solution of the lipase and with a non-ionic surfactant containing at least one fatty acid moiety and having an HLB-value of at least 8 to provide a supported lipase, thereafter washing the supported lipase and drying the washed lipase to obtain said immobilized lipase, said immobilized lipase containing 0.0001–5% of said surfactant based on the weight of said support containing said lipase immobilized thereon.

11. Process according to claim 10, wherein the aqueous solution of the lipase has a concentration of lipase up to the saturation concentration.

12. Process according to claim 10, wherein the hydrophobic support is contacted with an aqueous solution of the surfactant with a concentration of 0.01–10 wt. % of surfactant, said solution also containing dissolved lipase in an amount above zero up to its saturation concentration.

13. Process according to claim 10, wherein the contact time between aqueous lipase solution and support material varies from 1–72 hours.

14. Process according to claim 10, which comprises performing the contact between the support, and at least one of the lipase and the surfactant as a batch process, as a continuous process in a fixed bed, as a continuous process in a fluidized bed or in a continuously stirred tank, while the contacting is performed with a continuous motion of the lipase solution.

15. Process according to claim 10, wherein the hydrophobic support material has a water content of less than 1 wt. %.

* * * * *